(12) United States Patent
Hess et al.

(10) Patent No.: US 6,547,799 B2
(45) Date of Patent: Apr. 15, 2003

(54) VESSEL EVERSION INSTRUMENT WITH PRESSURIZABLE MEMBRANE

(75) Inventors: Christopher J. Hess, Lebanon, OH (US); Rudolph H. Nobis, Mason, OH (US); Michael F. Clem, Maineville, OH (US); Gary W. Knight, West Chester, OH (US); Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/891,587

(22) Filed: Jun. 26, 2001

(65) Prior Publication Data

US 2002/0198545 A1 Dec. 26, 2002

(51) Int. Cl.[7] .............................................. A61B 17/00
(52) U.S. Cl. ....................................................... 606/149
(58) Field of Search ................................. 606/149, 153, 606/151, 152, 148; 128/334, 334 R; 604/271; 623/1.14, 1.11, 1.13

(56) References Cited

U.S. PATENT DOCUMENTS

| 2,086,371 A | 7/1937 | Tear |
| 2,940,452 A | 6/1960 | Smialowski |
| 3,040,748 A | 6/1962 | Klein et al. |
| 3,057,355 A | 10/1962 | Smialowski et al. |
| 3,180,337 A | 4/1965 | Smialowski |
| 3,316,914 A | * 5/1967 | Collito ........................ 128/334 |
| 3,908,662 A | 9/1975 | Razgulov et al. |
| 4,144,631 A | * 3/1979 | Fujio ............................. 29/446 |
| 4,470,415 A | 9/1984 | Wozniak |
| 4,622,970 A | 11/1986 | Wozniak |
| 6,036,705 A | * 3/2000 | Nash et al. .................. 606/153 |
| 6,402,764 B1 | * 6/2002 | Hendricksen et al. |

* cited by examiner

Primary Examiner—John J. Calvert
Assistant Examiner—Alissa L. Hoey

(57) ABSTRACT

An instrument for everting an end of a vessel. The instrument has a tubular member having an axial bore, a distal end and a proximal end. The instrument further also has an elastic membrane sealably mounted on the distal end of the tubular member, a plunger slidably mounted within the axial bore of the body, a spring operationally engaged to the plunger for biasing the plunger in the distal direction and distending the membrane for insertion into the vessel, a distally extending mandrel mounted to the plunger, a sleeve slidably mounted over the membrane and at least a portion of the tubular member, and a proximal seal mounted in the proximal end of the axial bore so that the membrane, the proximal seal, and the axial bore define a sealed chamber. The instrument further comprises a pressure source for pressurizing the sealed chamber to expand the membrane into an expanded configuration, the sleeve limiting radial expansion of the membrane, and for depressurizing the sealed chamber to collapse the membrane into a collapsed configuration.

9 Claims, 4 Drawing Sheets

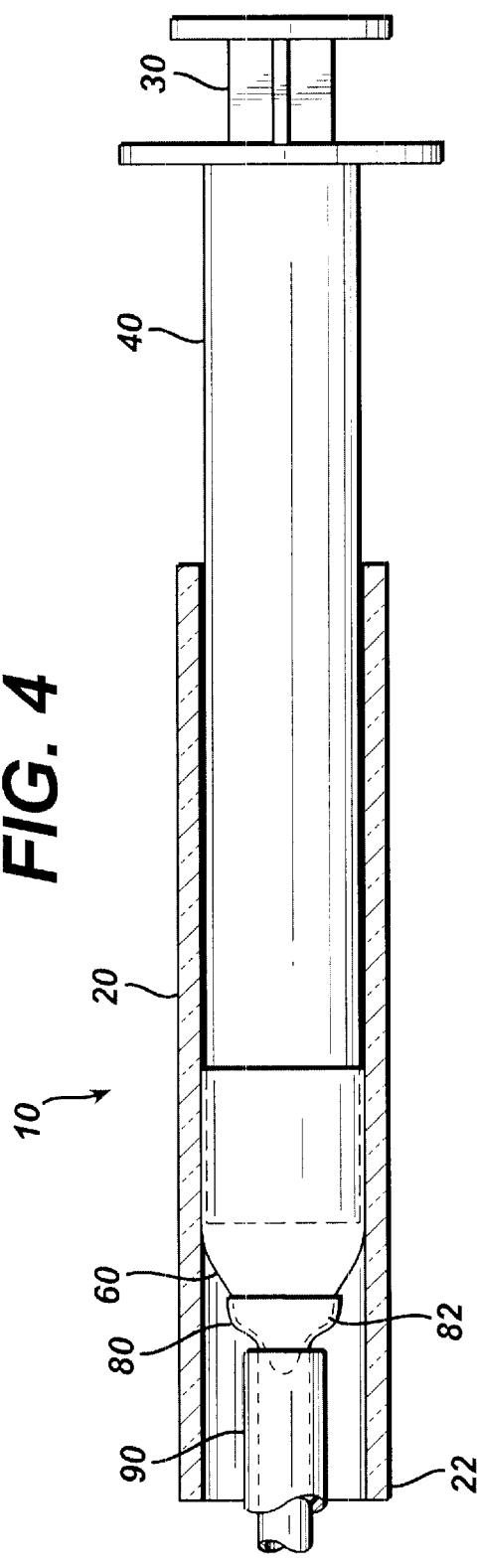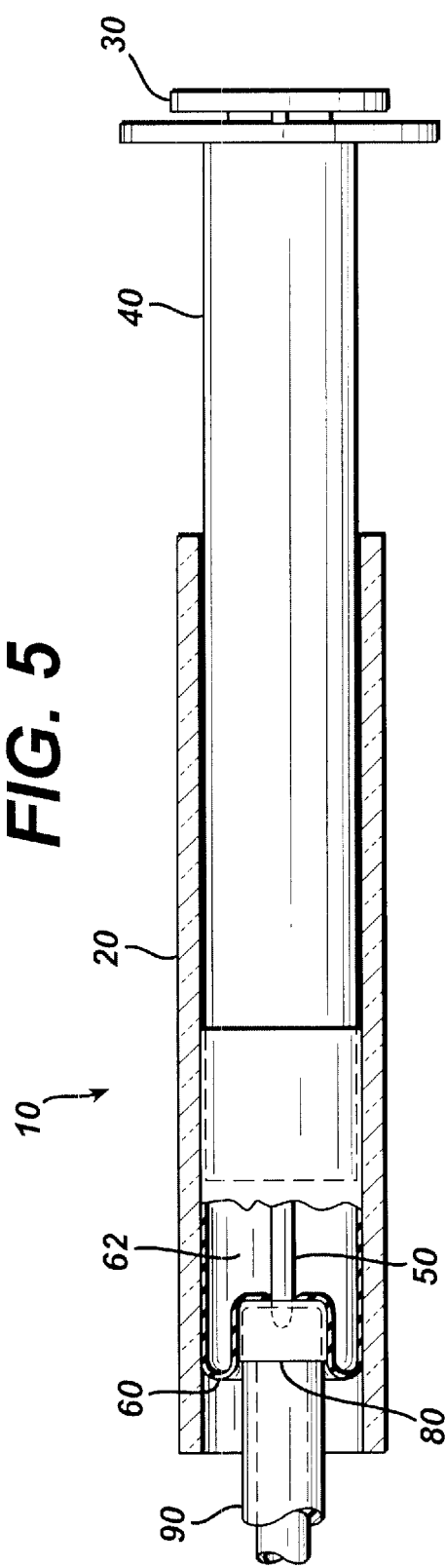

VESSEL EVERSION INSTRUMENT WITH PRESSURIZABLE MEMBRANE

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomoticsurgical procedures are common in the field of cardiac surgery. These procedures are conventionally used for repairing a damaged or diseased blood vessel. In a typical anastomotic procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (e.g., under 0.001 inch diameter) to suture the vessels together. The vessels may be joined end-to-end, end-to-side, or side-to-side. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as a segment of saphenous vein harvested from the patient) to a side of a target vessel (the stenosed coronary artery). For a proximal anastomosis in a conventional CABG procedure, the surgeon sutures a proximal end of the graft vessel to the side of the aorta.

As this field of art has progressed over the last several years, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (e.g., over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel, when the opposite end is already attached to the patient (e.g., at the distal anastomosis of a patient undergoing a CABG procedure). The eversion device should also allow for the proper length of everted tissue over the tube, bushing, or the like, depending on the requirements of the anastomosis device or method being used. Finally, it is desirable that the eversion device be low cost and yet operate reliably.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices which engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel.

Accordingly, an eversion instrument for everting an end of a vessel is disclosed. The instrument has a tubular member having an axial bore. The tubular member has a distal end and a proximal end, and a distal opening and a proximal opening in communication with the axial bore. An elastic membrane is sealably mounted on the distal end of the tubular member. The membrane has an inner side and an outer side. A plunger member is slidably mounted within said the axial bore of the tubular member. The plunger member has a distal end and a proximal end. There is a mandrel member that has a distal end and a proximal end. The proximal end of the mandrel member is mounted to the distal end of the plunger member, and the distal end of the mandrel member is in contact with the inner surface of the membrane. A spring is operationally engaged to the plunger for biasing the plunger in the distal direction and distending the membrane for insertion into an end of a vessel. A sleeve is slidably mounted over the membrane and at least a section of the tubular member. A proximal seal is mounted to the proximal end of the tubular member such that the proximal seal, the membrane and the axial bore define a sealed chamber having a volume. There is a pressure source mounted to the tubular member for pressurizing the sealed chamber to expand the membrane into an expanded configuration, and for depressurizing the sealed chamber to collapse the membrane into a collapsed configuration. The sleeve limits radial expansion of the membrane.

Yet another aspect of the present invention is a method of everting a vessel. An instrument is provided. The instrument has a tubular member having an axial bore. The tubular member has a distal end and a proximal end, and a distal opening and a proximal opening in communication with the axial bore. An elastic membrane is sealably mounted on the distal end of the tubular member. The membrane has an inner surface and an outer surface. A plunger member is slidably mounted within the axial bore of the tubular member. The plunger member has a distal end and a proximal end. A spring is operationally engaged to the plunger for biasing the plunger in the distal direction and for distending the membrane for insertion into an end of a vessel. There is a mandrel member having a distal end and a proximal end. The proximal end of the mandrel member is mounted to the distal end of the plunger member, and the distal end of the mandrel member in contact with the inner surface of the membrane. A sleeve is slidably mounted over the membrane and at east a section of the tubular member. A proximal seal is mounted to the proximal end of the tubular member such that the proximal seal, the membrane and the axial bore define a sealed chamber having a volume. A pressure source is mounted to the tubular member for pressurizing the sealed chamber to expand the membrane into an expanded configuration, and for depressurizing the sealed chamber to collapse said membrane into a collapsed configuration. The sleeve limits radial expansion of the membrane.

A tubular workpiece is provided. The tubular workpiece has an inner lumen, a proximal end, a distal end, and an inner surface and an outer surface. A vessel is provided. The vessel has a distal end, a proximal end, an inner lumen, and an inner surface and an outer surface. The vessel mounted in the lumen of the tubular workpiece;

The membrane is inserted into the lumen of the vessel while the instrument is in a depressurized mode such that the outer surface of the membrane is in contact with the inner surface of the vessel. The instrument is pressurized to an intermediate positive pressure mode. The sleeve is moved over the vessel and tubular member. The instrument is then pressurized to a full positive pressure mode, thereby everting the distal end of the vessel over the distal end of the tubular workpiece such that the outer surface of the distal end of the vessel is in contact with the outer surface to the distal end of the tubular workpiece. Finally, the instrument is depressurized to a negative pressure mode and removing the instrument from the vessel and tubular workpiece.

Yet another aspect of the present invention is a system for everting a vessel. The system is the combination of the above-described instrument and tubular workpiece.

These and other aspects and advantages of the present invention will become more apparent from the following description and accompanying drawings.

BRIEF DESCRIPTION OF THE DRAWINGS

FIG. 4 is a partial cross-sectional side view showing eversion instrument 10 in an intermediate positive pressurized mode and sleeve 20 in the extended position;

FIG. 5 is a partial cross-sectional side view of eversion instrument 10 in a full positive pressurized mode and sleeve 20 in the extended position with vessel end 82 everted.

DETAILED DESCRIPTION OF THE INVENTION

Figure 1:
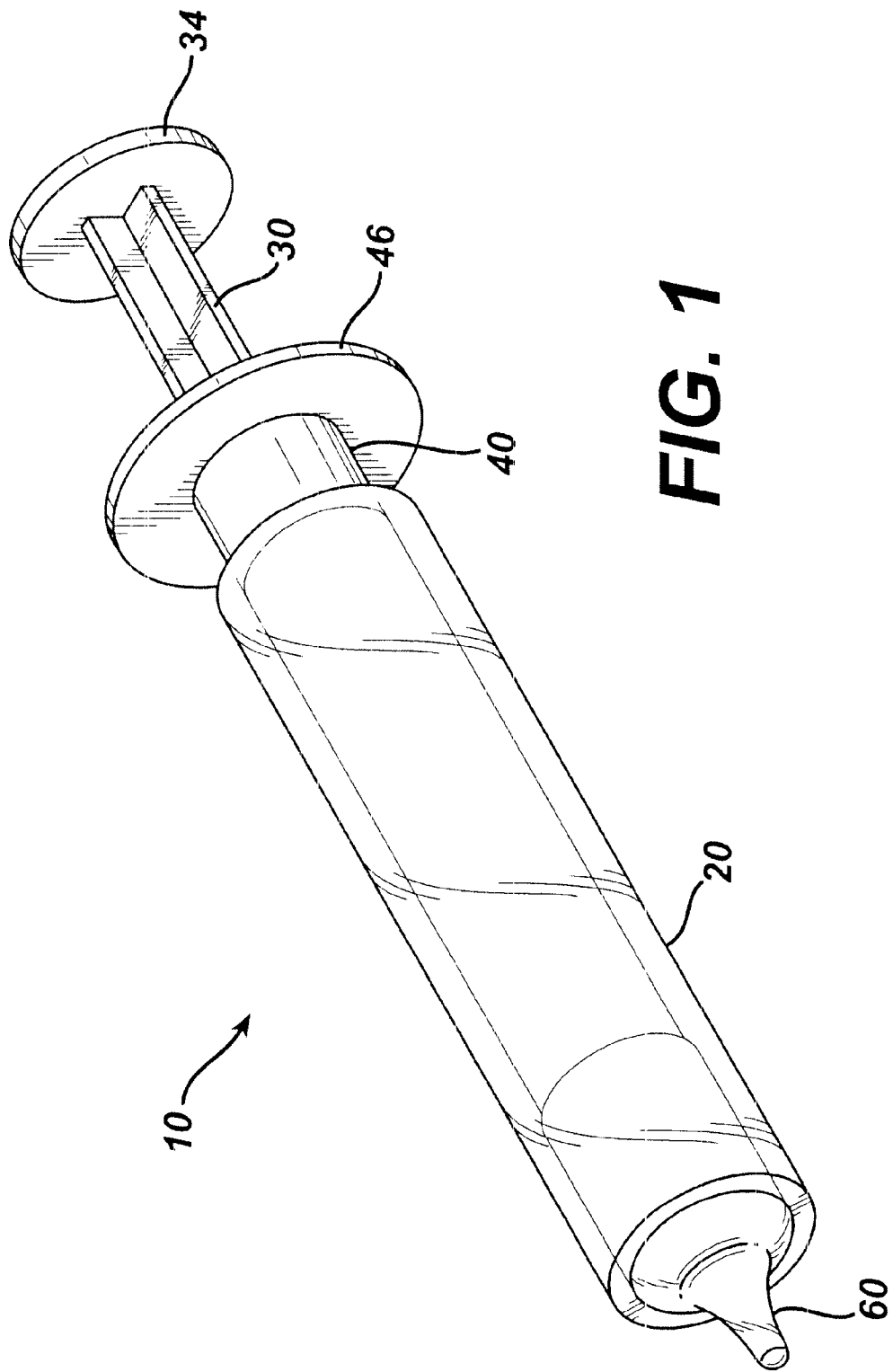
FIG. 1 is an isometric view of an eversion instrument 10 of the present invention.
Figure 2:
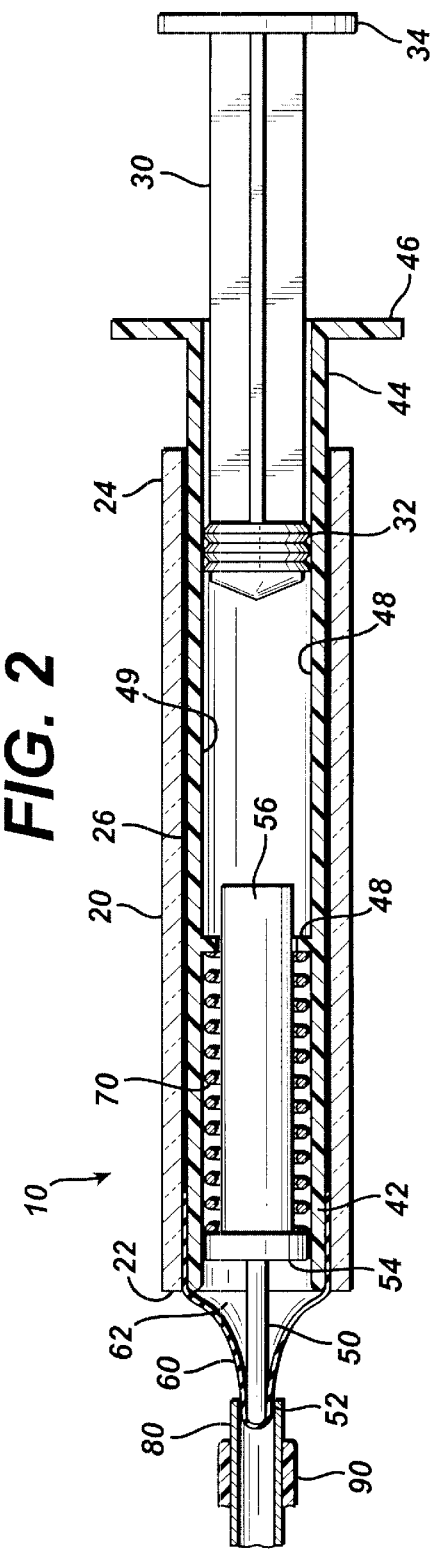
FIG. 2 is a cross-sectional side view of the eversion instrument 10 of FIG. 1 in a depressurized mode and a sleeve 20 in a retracted position and engaging the end of a blood vessel prior to eversion.

The eversion instrument 10 of the present invention is illustrated in FIGS. 1 and 2. Instrument 10 is seen to have a tubular frame 40 having a flange 46 and mounted slidably inside of a sleeve 20. A plunger 30 is seen to slidably mounted in axial bore 49 of frame 10. Mounted to the distal end 42 of tubular frame 40 is a membrane 60. These features will be described in more detail below. Eversion instrument 10 is approximately the same size and looks much like a medical syringe for administering fluids. Eversion instrument 10 is preferably single patient use, disposable, and the materials disclosed in the present embodiment are sterilizable using conventional gamma radiation, ethylene oxide, or other sterilization methods, although it is possible to construct eversion instrument 10 to be a reusable, steam autoclavable instrument, as will be apparent to those skilled in the art.

Figure 3:
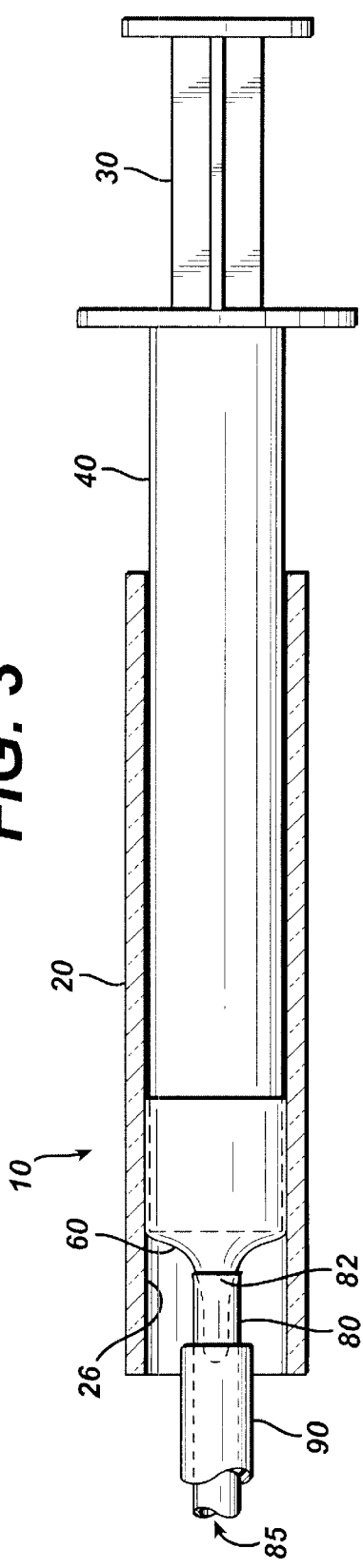
FIG. 3 is a partial cross-sectional side view showing eversion instrument 10 in a depressurized mode and having a sleeve 20 moved to an extended position.

Referring to FIG. 2, eversion instrument 10 is shown in a depressurized mode. Tubular frame 40 is seen to have a distal end 42, a proximal end 44, and an axial bore 49 therethrough. Tubular frame 40 is preferably made from a rigid or semi-rigid, conventional biocompatible material, including metals, ceramics and polymers and combinations thereof, e.g., polyethylene or polypropylene. Sleeve 20 is seen to have a distal end 22, a proximal end 24, and an axial bore 26 therethrough that fits closely over tubular frame 40 such that sleeve 20 is slidable over frame 40. An operator may grasp sleeve 20 and move it in either the proximal or distal directions over tubular frame 40, between a retracted position as shown in FIG. 2 and an extended position as shown in FIG. 3. Sleeve 20 is rigid and preferably constructed from a transparent, conventional biocompatible material such as, for example, polycarbonate in order to view the inside during operation. A plunger 30 comprises a seal 32 that fits sealably inside of axial bore 49 of proximal end 44 of tubular frame 40. The axial position of plunger 30 relative to tubular frame 40 is adjustable by pushing a pad 34 of plunger 30 close to flange 46 on tubular frame 40, or by pulling pad 34 away from flange 46. A membrane 60 made from a conventional biocompatible elastic material such as latex rubber is mounted to distal end 42 of tubular frame 40. An internal chamber 62 is formed within the enclosed space within axial bore 49 of tubular frame 40. Chamber 62 preferably contains only air, but may contain a conventional biocompatible, hydraulic fluid such as, for example, saline. When the operator pushes plunger 30 in the distal direction, the pressure inside of chamber 62 increases; when the operator pulls plunger 30 in the proximal direction, the pressure inside of chamber 62 decreases.

Still referring to FIG. 2, a piston 56 is seen to be mounted inside the axial bore 49 at the distal end 42 of tubular frame 40. A compression spring 70 is mounted over piston 56 and between a retainer 54 on piston 56 and a stop 48 extending radially into axial bore 49 of tubular frame 40 to bias piston 56 in the distal direction. Compression spring 70 is preferably made from a stainless steel. A mandrel 50 is coaxially mounted to retainer 54 of piston 56 and comprises a rounded, distal tip 52 that engages and stretches membrane 60 into a nipple shape for insertion into the lumen of the end of a vessel 80 to be everted. Piston 56 and mandrel 50 are preferably made from a rigid plastic. Vessel 80 is held in a tubular workpiece 90, which may be a tube, ferrule, bushing, anastomotic coupler, or other device required for performing the anastomosis of vessel 80 to another vessel.

FIG. 3 is a partial sectional side view of eversion instrument 10 in a depressurized mode. In order to evert end 82 of vessel 80 using the eversion instrument 10 of the present invention, the user axially positions plunger 30 inside of tubular frame 40 so that the pressure inside eversion instrument 10 is approximately equal to ambient pressure. The user then inserts the stretched, distal portion of membrane 60 into lumen 85 of vessel 80, which is held by tubular workpiece 90. The user next manually slides sleeve 20 over the end 82 of vessel 80 and the end 92 of tubular workpiece 90, preferably after inserting membrane 60 into vessel 80.

The user then pushes plunger 30 distally into tubular frame 40 to inflate partially membrane 60 as seen in FIG. 4, which illustrates instrument 10 in the intermediate positive pressurized mode. Vessel end 82 of vessel 80 conforms to the shape of partially inflated membrane 60 inserted in vessel end 82 of vessel 80. During this step, the user positions distal end 22 of sleeve 20 over tube 90.

As seen in FIG. 5, the eversion instrument 10 is in the full positive pressurized mode when the pressure inside of chamber 62 reaches its highest level during the operational sequence. The user pushes plunger 30 completely into tubular frame 40 to fully inflate membrane 60. As the user pushes plunger 30 distally to the position shown, the applied force in the distal direction aids in rolling membrane 60 over tubular workpiece 90 and everting vessel 80 over the end of tubular workpiece 90. Mandrel 50 helps to hold membrane 60 against vessel 80 and tubular workpiece 90 with a predetermined force supplied by compression spring 70 (shown in FIG. 2).

Figure 6:
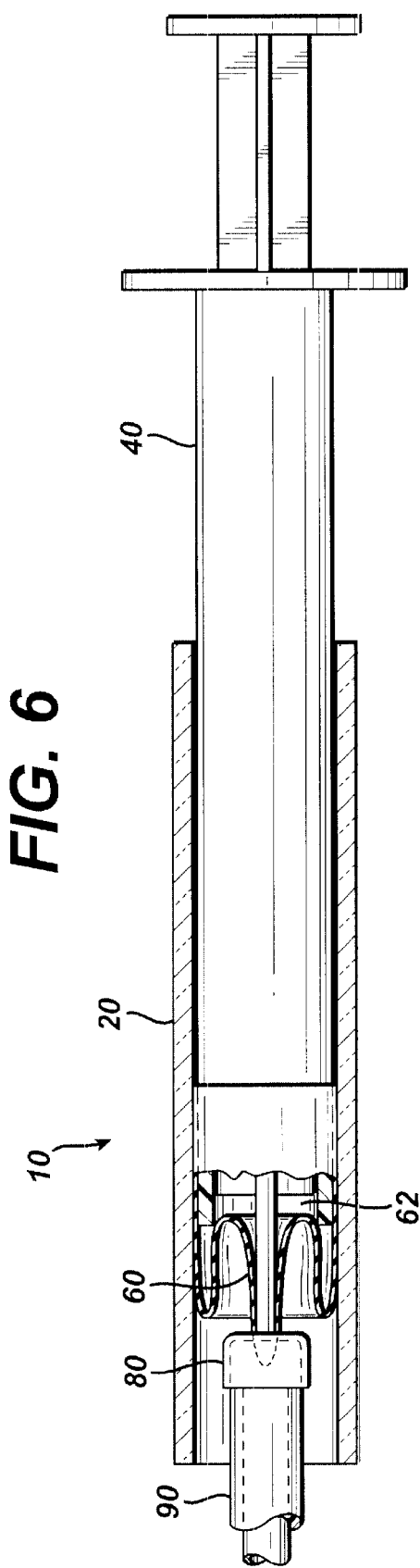
FIG. 6 is a partial cross-sectional side view of eversion instrument 10 in a negative pressurized mode and sleeve 20 in the extended position with end 82 of vessel 80 everted.

FIG. 6 illustrates eversion instrument 10 in the negative pressurized mode. The user pulls plunger 30 proximally from tubular frame 40 while holding sleeve 20 in the extended position as shown, thus lowering the pressure inside chamber 62 to below ambient pressure, and causing membrane 60 to collapse and pull away from vessel 80 and tubular workpiece 90. The user may next withdraw eversion instrument 10 from vessel 80 and tubular workpiece 90 without disturbing the eversion of vessel 80. The user may inspect vessel 80, and if not satisfied with the eversion, repeat the steps described for FIGS. 2–6.

The following example is illustrative of the principles and practice of the present invention, although not limited thereto.

EXAMPLE

A patient undergoing cardiac coronary artery bypass graft (CABG) surgery is prepared for surgery and anesthetized in a conventional manner in accordance with the prevailing medical standards. The patient's chest is opened in a conventional manner by cutting through the sternum and expanding the rib cage with a conventional surgical retractor instrument. The patient's heart is accessed in a conventional manner and the patient is connected to a pulmonary bypass machine and the heart is stopped. A section of the patient's saphenous vein, which has already been harvested by this time, is prepared for use as a graft vessel. The graft vessel end that is to be attached to the aorta for the proximal anastomosis is everted using an eversion instrument of the present invention as already described in the detailed description and shown in FIGS. 2–6. In FIG. 6, vessel 80 is shown everted over tube 90. One embodiment of tube 90 is disclosed in published patent application WO0056228, "Low Profile Anastomosis Connector", filed on Mar. 20, 2000, assigned to By-Pass, Inc., and which is hereby incorporated herein by reference. As described in WO0056228, a metallic anastomosis connector comprising a plurality of ring segments is used to fastens the graft vessel to another vessel such as the aorta. The distal end of the graft vessel is then anastomotically attached to a coronary artery on the heart using a conventional hand suturing method. Additional bypasses are performed in the same manner or variations, depending on the patient's condition and anatomy. The remainder of the CABG procedure is conducted in a conventional manner and includes the steps of inspecting and repairing the grafts for leaks, checking blood flow, removing the patient from the pulmonary bypass machine, and closing the surgical incision.

The eversion instruments and eversion methods of the present invention have many advantages. The present invention is less traumatic to the intima of the vessel during the eversion procedure than conventional surgical graspers and the like. The present invention is easy for the surgeon to use without assistance and requires only a few steps to operate. The present invention is useful for a wide range of blood vessel sizes, particularly small vessels, e.g., having a diameter of about 2–3 mm or less. In addition, the present invention is useful on one end of a vessel, when the opposite end is already attached to the patient (e.g., at the distal anastomosis of a patient undergoing a CABG procedure). The present invention also allows for the proper length of everted tissue over the tube, bushing, or the like, depending on the requirements of the anastomosis device or method being used. Finally, the present invention may be manufactured inexpensively.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

Although this invention has been shown and described with respect to detailed embodiments thereof, it will be understood by those skilled in the art that various changes in form and detail thereof may be made without departing from the spirit and scope of the claimed invention.

What is claimed is:

1. An instrument for everting an end of a vessel over an end of a tubular workpiece, said instrument comprising:
    a tubular member having an axial bore, the tubular member having a distal end and a proximal end, and the tubular member having a distal opening and a proximal opening in communication with the axial bore;
    an elastic membrane sealably mounted on the distal end of the tubular member, the membrane having an inner side and an outer side;
    a plunger member slidably mounted within said the axial bore of the tubular member, the plunger member having a distal end and a proximal end;
    a mandrel member having a distal end and a proximal end, the proximal end of the mandrel member mounted to the distal end of the plunger member, the distal end of the mandrel member in contact with the inner surface of the membrane;
    a spring operationally engaged to the plunger for biasing the plunger in the distal direction and distending the membrane for insertion into an end of a vessel;
    a sleeve slidably mounted over said membrane and at least a section of the tubular member;
    a proximal seal mounted to the proximal end of the tubular member such that the proximal seal, the membrane and the axial bore define a sealed chamber having a volume; and, a pressure source mounted to the tubular member for pressurizing the sealed chamber to expand the membrane into an expanded configuration, and for depressurizing said sealed chamber to collapse said membrane into a collapsed configuration, wherein the sleeve limits radial expansion of the membrane.

2. The instrument of claim 1, wherein the sleeve comprises a transparent plastic.

3. The instrument of claim 1, wherein the membrane comprises latex rubber.

4. The instrument of claim 1, wherein the proximal seal is operable as the pressure source, the proximal seal being movable within the axial bore so that the volume of said sealed chamber may be manually increased and decreased.

5. A method for everting an end of a vessel over an end of a tubular workpiece, said method comprising the steps:

providing an instrument comprising:
   a tubular member having an axial bore, the tubular member having a distal end and a proximal end, and the tubular member having a distal opening and a proximal opening in communication with the axial bore;
   an elastic membrane sealably mounted on the distal end of the tubular member, the membrane having an inner surface and an outer surface;
   a plunger member slidably mounted within said the axial bore of the tubular member, the plunger member having a distal end and a proximal end;
   a spring operationally engaged to the plunger for biasing the plunger in the distal direction and distending the membrane for insertion into an end of a vessel;
   a mandrel member having a distal end and a proximal end, the proximal end of the mandrel member mounted to the distal end of the plunger member, the distal end of the mandrel member in contact with the inner surface of the membrane;
   a sleeve slidably mounted over said membrane and at least a section of the tubular member;
   a proximal seal mounted to the proximal end of the tubular member such that the proximal seal, the membrane and the axial bore define a sealed chamber having a volume; and,
   a pressure source mounted to the tubular member for pressurizing the sealed chamber to expand the membrane into an expanded configuration, and for depressurizing said sealed chamber to collapse said membrane into a collapsed configuration, wherein the sleeve limits radial expansion of the membrane;

providing a tubular workpiece having an inner lumen, a proximal end, a distal end, and an outer surface;

providing a vessel having a distal end, a proximal end, and an inner lumen, and an inner surface and an outer surface, said vessel mounted in the lumen of the tubular workpiece;

inserting the membrane into the lumen of a vessel while the instrument is in a depressurized mode such that the outer surface of the membrane is in contact with the inner surface of the vessel;

pressurizing said instrument to an intermediate positive pressure mode;

moving the sleeve over the vessel and tubular member;

pressurizing the instrument to a full positive pressure mode, thereby everting the distal end of the vessel over the distal end of the tubular workpiece such that the outer surface of the distal end of the vessel is in contact with the outer surface to the distal end of the tubular workpiece; and depressurizing the instrument to a negative pressure mode and removing the instrument from the vessel and tubular workpiece.

6. A system for everting a vessel, comprising the combination of:

I. an instrument comprising:
   a tubular member having an axial bore, the tubular member having a distal end and a proximal end, and the tubular member having a distal opening and a proximal opening in communication with the axial bore;
   an elastic membrane sealably mounted on the distal end of the tubular member, the membrane having an inner surface and an outer surface;
   a plunger member slidably mounted within said the axial bore of the tubular member, the plunger member having a distal end and a proximal end;
   a spring operationally engaged to the plunger for biasing the plunger in the distal direction and distending the membrane for insertion into an end of a vessel;
   a mandrel member having a distal end and a proximal end, the proximal end of the mandrel member mounted to the distal end of the plunger member, the distal end of the mandrel member in contact with the inner surface of the membrane;
   a sleeve slidably mounted over said membrane and at least a section of the tubular member;
   a proximal seal mounted to the proximal end of the tubular member such that the proximal seal, the membrane and the axial bore define a sealed chamber having a volume; and,
   a pressure source mounted to the tubular member for pressurizing the sealed chamber to expand the membrane into an expanded configuration, and for depressurizing said sealed chamber to collapse said membrane into a collapsed configuration, wherein the sleeve limits radial expansion of the membrane; and, II. a tubular workpiece comprising a tube having an inner lumen, a proximal end, a distal end, an outer surface, an inner surface and proximal and distal openings in communication with the inner lumen.

7. The system of claim 6, wherein the sleeve comprises a transparent plastic.

8. The system of claim 6, wherein the membrane comprises latex rubber.

9. The system of claim 6, wherein the proximal seal is operable as the pressure source, the proximal seal being movable within the axial bore so that the volume of said sealed chamber may be manually increased and decreased.

* * * * *